(12) United States Patent
Hansen et al.

(10) Patent No.: US 11,166,627 B2
(45) Date of Patent: Nov. 9, 2021

(54) METHOD FOR FIXATION OF A WIRE PORTION OF AN ENDOSCOPE, AND AN ENDOSCOPE

(71) Applicant: AMBU A/S, Ballerup (DK)

(72) Inventors: Michael Kappler Hansen, Vallensbæk (DK); Jesper Grøndahl Lund, Ballerup (DK)

(73) Assignee: AMBU A/S, Ballerup (DK)

( * ) Notice: Subject to any disclaimer, the term of this patent is extended or adjusted under 35 U.S.C. 154(b) by 528 days.

(21) Appl. No.: 16/251,071

(22) Filed: Jan. 17, 2019

(65) Prior Publication Data
US 2019/0231179 A1 Aug. 1, 2019

(30) Foreign Application Priority Data

Jan. 26, 2018 (EP) .................................... 18153615

(51) Int. Cl.
| | | |
|---|---|---|
| *A61B 1/00* | (2006.01) | |
| *A61B 1/018* | (2006.01) | |
| *A61B 1/005* | (2006.01) | |
| *A61B 1/008* | (2006.01) | |

(Continued)

(52) U.S. Cl.
CPC .............. *A61B 1/018* (2013.01); *A61B 1/008* (2013.01); *A61B 1/0011* (2013.01); *A61B 1/0057* (2013.01); *A61B 1/0055* (2013.01); *A61B 1/00137* (2013.01); *A61B 1/05* (2013.01); *A61B 1/0684* (2013.01)

(58) Field of Classification Search
None
See application file for complete search history.

(56) References Cited

U.S. PATENT DOCUMENTS

| 609,570 A | * | 8/1898 | Bowden | .................... F16C 1/26 74/502.5 |
|---|---|---|---|---|
| 2,849,548 A | | 8/1958 | Young | |
| 3,958,566 A | | 5/1976 | Furihata | |

(Continued)

FOREIGN PATENT DOCUMENTS

| AU | 2008/207558 | 4/2009 |
|---|---|---|
| CN | 1692872 | 11/2005 |

(Continued)

OTHER PUBLICATIONS

European Search Report issued by the European Patent Office, dated Jul. 23, 2018 in related European Patent Application No. 18153615; 7 pages.

*Primary Examiner* — Timothy J Neal
(74) *Attorney, Agent, or Firm* — Faegre Drinker Biddle & Reath LLP

(57) ABSTRACT

An endoscope made by a method for fixation of portions of a steering wire of the endoscope, the steering wire having a first portion, a second portion, and a third portion, the first portion connected to a steerable tip and the second portion connected to a control element, the method including pulling the third portion so as to tension the steering wire and inserting a pin with a wire guide into a pin spacing so that so that the second portion is positioned in the wire guide and is clamped between the pin and at least one wall of the control element, whereby the pin and the second portion are fixated to the control element to thereby maintain a wire tension between the first and second portions.

18 Claims, 9 Drawing Sheets

(51) Int. Cl.
  *A61B 1/05* (2006.01)
  *A61B 1/06* (2006.01)

(56) References Cited

U.S. PATENT DOCUMENTS

| | | | |
|---|---|---|---|
| 4,203,430 A | 5/1980 | Takahashi |
| 4,745,908 A | 5/1988 | Wardle |
| 4,750,475 A | 6/1988 | Yoshihashi |
| 4,757,827 A | 7/1988 | Buchbinder |
| 4,805,596 A | 2/1989 | Hatori |
| 4,832,473 A | 5/1989 | Ueda |
| 4,926,172 A | 5/1990 | Gorsek |
| 5,122,125 A | 6/1992 | Deuss |
| 5,167,221 A | 12/1992 | Chikama |
| 5,170,775 A | 12/1992 | Tagami |
| 5,179,934 A | 1/1993 | Nagayoshi et al. |
| 5,275,151 A | 1/1994 | Shockey |
| 5,299,562 A | 4/1994 | Heckele |
| 5,327,881 A | 7/1994 | Greene |
| 5,347,989 A | 9/1994 | Monroe et al. |
| 5,429,620 A | 7/1995 | Davis |
| 5,462,527 A | 10/1995 | Stevens-Wright et al. |
| 5,512,035 A | 4/1996 | Konstorum et al. |
| 5,541,622 A | 7/1996 | Engle et al. |
| 5,544,902 A | 8/1996 | Belter |
| 5,607,386 A | 3/1997 | Flam |
| 5,626,553 A | 5/1997 | Frassica et al. |
| 5,643,174 A | 7/1997 | Yamamoto et al. |
| 5,785,663 A | 7/1998 | Sarvazyan |
| 5,810,876 A | 9/1998 | Kelleher |
| 5,879,289 A | 3/1999 | Yarush |
| 5,888,192 A | 3/1999 | Heimberger |
| 5,889,507 A | 3/1999 | Engle et al. |
| 5,913,816 A | 6/1999 | Sanders et al. |
| 5,938,588 A | 8/1999 | Grabover |
| 6,007,531 A | 12/1999 | Snoke |
| 6,117,071 A | 9/2000 | Ito et al. |
| 6,200,294 B1 | 3/2001 | Liu |
| 6,236,034 B1 | 5/2001 | DeVolpi |
| 6,258,101 B1 | 7/2001 | Blake, III |
| 6,270,508 B1 | 8/2001 | Klieman |
| 6,440,062 B1 | 8/2002 | Ouchi |
| 6,569,086 B2 | 5/2003 | Motoki et al. |
| 6,821,157 B2 | 11/2004 | Brändström et al. |
| 6,829,497 B2 | 12/2004 | Mogul |
| 7,300,438 B2 | 11/2007 | Falwell et al. |
| 7,524,301 B2 | 4/2009 | Dubois et al. |
| 7,591,784 B2 | 9/2009 | Butler |
| 7,662,092 B2 | 2/2010 | Miyagi et al. |
| 7,794,392 B2 | 9/2010 | Maruyama |
| 7,828,725 B2 | 11/2010 | Maruyama |
| 7,934,505 B2 | 5/2011 | Garren et al. |
| 8,449,530 B2 | 5/2013 | Bacher et al. |
| 8,790,250 B2 | 4/2014 | Petersen |
| 8,821,389 B2 | 9/2014 | Yamane |
| 9,125,582 B2 | 9/2015 | Petersen |
| 9,162,036 B2 | 10/2015 | Caples et al. |
| 10,149,605 B2 | 12/2018 | Petersen et al. |
| 2001/0023313 A1 | 9/2001 | Ide |
| 2001/0025135 A1 | 9/2001 | Naito et al. |
| 2002/0099266 A1 | 7/2002 | Ogura |
| 2003/0009176 A1 | 1/2003 | Bilitz |
| 2003/0092965 A1 | 5/2003 | Konomura et al. |
| 2004/0019256 A1 | 1/2004 | Cubb et al. |
| 2004/0220449 A1 | 11/2004 | Zirps et al. |
| 2004/0267093 A1 | 12/2004 | Miyagi et al. |
| 2005/0070764 A1 | 3/2005 | Nobis |
| 2005/0075539 A1 | 4/2005 | Schulz et al. |
| 2005/0131279 A1 | 6/2005 | Boulais et al. |
| 2005/0197536 A1 | 9/2005 | Banik et al. |
| 2006/0025651 A1 | 2/2006 | Adler |
| 2006/0258955 A1 | 11/2006 | Hoffman |
| 2007/0219411 A1 | 9/2007 | Dejima |
| 2007/0232858 A1 | 10/2007 | Macnamara et al. |
| 2007/0255104 A1 | 11/2007 | Maruyama |
| 2007/0282167 A1 | 12/2007 | Barenboym et al. |
| 2007/0299311 A1 | 12/2007 | Sato et al. |
| 2008/0051631 A1 | 2/2008 | Dejima et al. |
| 2008/0051694 A1 | 2/2008 | Kato |
| 2008/0188868 A1 | 8/2008 | Weitzner et al. |
| 2008/0195128 A1 | 8/2008 | Orbay |
| 2008/0249362 A1 | 10/2008 | Jiang et al. |
| 2008/0287735 A1 | 11/2008 | Takemoto |
| 2009/0054733 A1 | 2/2009 | Marescaux |
| 2009/0076328 A1 | 3/2009 | Root |
| 2009/0143647 A1 | 6/2009 | Banju |
| 2009/0247994 A1 | 10/2009 | Bacher et al. |
| 2010/0022837 A1 | 1/2010 | Ishiguro |
| 2010/0030020 A1 | 2/2010 | Sanders |
| 2010/0063512 A1 | 3/2010 | Braga et al. |
| 2010/0106103 A1 | 4/2010 | Ziebol et al. |
| 2010/0121147 A1 | 5/2010 | Oskin et al. |
| 2010/0249497 A1 | 9/2010 | Peine |
| 2010/0249639 A1 | 9/2010 | Bhatt |
| 2010/0268268 A1 | 10/2010 | Bacher |
| 2010/0298642 A1 | 11/2010 | Trusty |
| 2011/0009694 A1 | 1/2011 | Schultz |
| 2011/0264129 A1 | 10/2011 | Holdgate |
| 2011/0306831 A1 | 12/2011 | Køhnke et al. |
| 2012/0220828 A1 | 8/2012 | Iwasaki et al. |
| 2013/0074303 A1 | 3/2013 | Durrant et al. |
| 2013/0137924 A1 | 5/2013 | Iwasaki et al. |
| 2013/0204082 A1 | 8/2013 | Fischer, Jr. |
| 2013/0281782 A1 | 10/2013 | Zhou |
| 2014/0046123 A1 | 2/2014 | Connors et al. |
| 2014/0073855 A1 | 3/2014 | Kindler |
| 2014/0142377 A1 | 5/2014 | Yang |
| 2014/0148759 A1 | 5/2014 | Macnamara et al. |
| 2014/0206936 A1 | 7/2014 | Cooper et al. |
| 2014/0243615 A1 | 8/2014 | Schaeffer et al. |
| 2014/0257249 A1 | 9/2014 | Witt |
| 2014/0275763 A1 | 9/2014 | King et al. |
| 2014/0336532 A1 | 11/2014 | Seguy |
| 2015/0216644 A1 | 8/2015 | Cahill et al. |
| 2015/0217092 A1 | 8/2015 | Kokate et al. |
| 2015/0335227 A1 | 11/2015 | Jacobsen et al. |
| 2015/0366435 A1 | 12/2015 | Williams |
| 2017/0119481 A1 | 5/2017 | Romo et al. |
| 2017/0281296 A1 | 10/2017 | Cooper et al. |
| 2018/0296068 A1 | 10/2018 | Matthison-Hansen et al. |
| 2018/0296069 A1 | 10/2018 | Matthison-Hansen et al. |
| 2018/0303315 A1 | 10/2018 | Matthison-Hansen et al. |
| 2018/0303316 A1 | 10/2018 | Matthison-Hansen et al. |
| 2018/0303317 A1 | 10/2018 | Matthison-Hansen et al. |
| 2018/0303472 A1 | 10/2018 | Matthison-Hansen et al. |
| 2018/0309908 A1 | 10/2018 | Matthison-Hansen et al. |
| 2019/0110661 A1* | 4/2019 | Do ................. A61B 1/0052 |

FOREIGN PATENT DOCUMENTS

| | | |
|---|---|---|
| CN | 102271571 | 12/2011 |
| EP | 0357274 | 3/1990 |
| EP | 0567146 | 10/1993 |
| EP | 1046406 | 10/2000 |
| EP | 1484003 | 8/2004 |
| EP | 1561413 | 8/2005 |
| EP | 2067433 | 6/2009 |
| EP | 2106751 | 7/2009 |
| EP | 2288284 A2 | 3/2011 |
| JP | S4991184 | 11/1947 |
| JP | H0666619 | 3/1994 |
| JP | H0910166 | 1/1997 |
| JP | H11216103 | 8/1999 |
| JP | 2003052618 | 2/2003 |
| JP | 2004321612 | 11/2004 |
| JP | 2005237608 | 9/2005 |
| JP | 4210451 | 1/2009 |
| JP | 2013008610 A | 1/2013 |
| WO | WO 2005/112806 | 12/2005 |
| WO | WO 2007/092636 | 8/2007 |
| WO | WO 2008/033356 | 3/2008 |
| WO | WO 2008/045374 | 4/2008 |
| WO | WO 2008/061106 | 5/2008 |
| WO | WO 2009/140288 A2 | 11/2009 |

(56) References Cited

FOREIGN PATENT DOCUMENTS

| | | |
|---|---|---|
| WO | WO 2009/140288 A3 | 11/2009 |
| WO | WO 2010/066789 | 6/2010 |
| WO | WO 2010/066790 | 7/2010 |
| WO | WO 2013/071938 | 5/2013 |
| WO | WO 2013/106444 | 7/2013 |
| WO | WO 2014/127780 | 8/2014 |
| WO | WO 2016/188537 A1 | 12/2016 |
| WO | WO 2016/188538 A1 | 12/2016 |
| WO | WO 2017/167713 | 10/2017 |

* cited by examiner

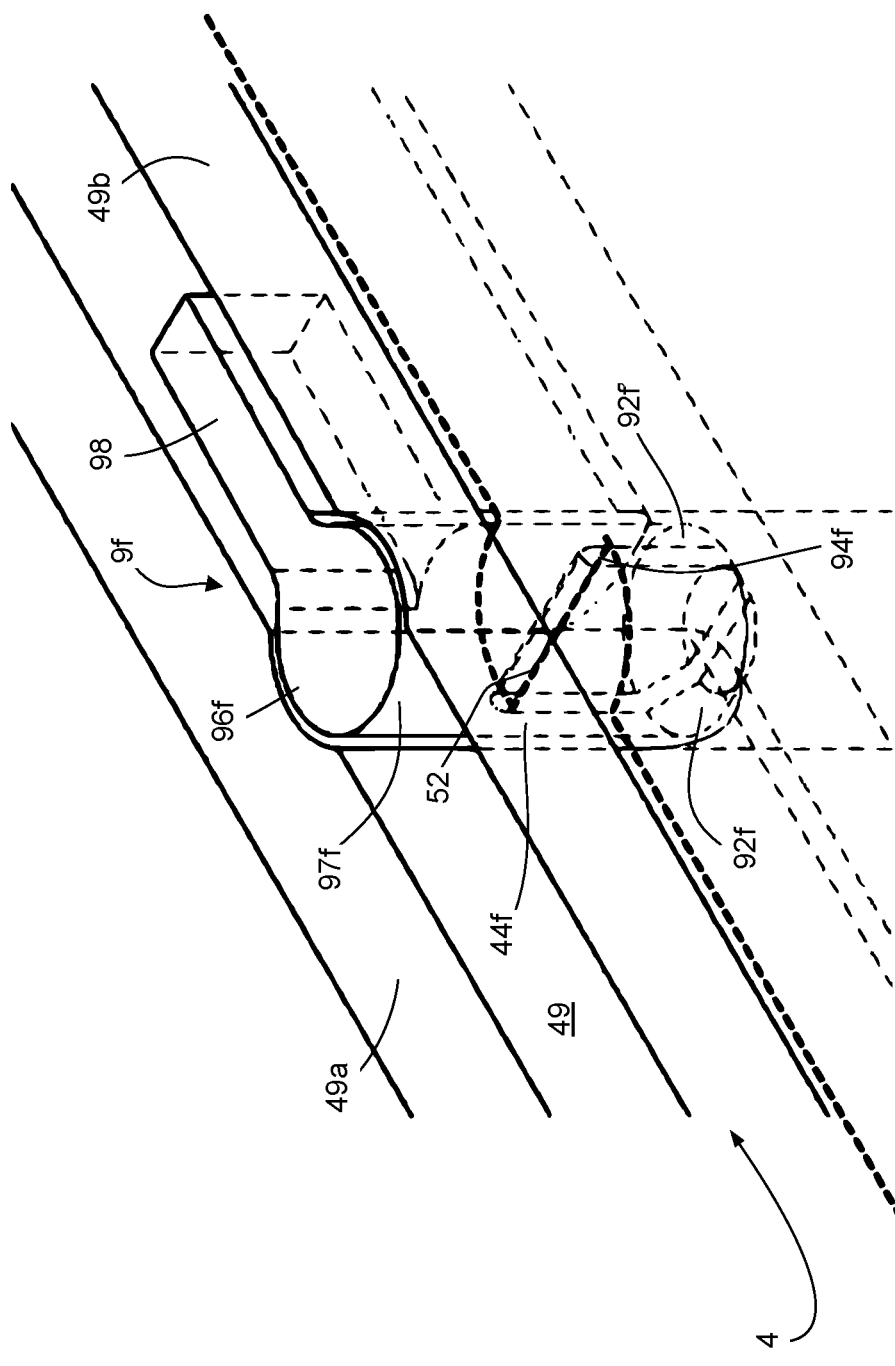

METHOD FOR FIXATION OF A WIRE PORTION OF AN ENDOSCOPE, AND AN ENDOSCOPE

CROSS-REFERENCE TO RELATED APPLICATIONS

This application claims the benefit of Europe Patent Application No. EP18153615.2, filed Jan. 26, 2018, which is expressly incorporated herein by reference in its entirety.

TECHNICAL FIELD

The present disclosure relates to steerable endoscopes, and more specifically to a method for fixation of a steering wire.

BACKGROUND

Endoscopes are well known inspection devices. An endoscope comprises an insertion tube attached to a handle, and visual inspections means, such as a built-in camera, at a distal end of the endoscope. Electrical wiring for the camera and other electronics such as LED lighting typically runs along an inside of the insertion tube from the handle to the tip at the distal end. Instead of using cameras, endoscopes may also be fibre-optic, in which case optical fibres typically run along an inside of the insertion tube. A working channel may run along the inside of the insertion tube from the handle to the tip, e.g. allowing liquid to be removed from the body cavity or allowing for insertion of surgical instruments or the like into the body cavity.

In order to be able to maneuver a camera or the like of the endoscope inside the body cavity, the distal end of the endoscope may, in addition to the camera, comprise a section with increased flexibility, specifically an articulated or bendable tip allowing the operator to bend this section to thereby move the camera. Typically, maneuvering is carried out by tensioning or slacking steering wires in a guide tube also running along the inside of the elongated insertion tube from the articulated tip to a control element with an operating member in the handle in an arrangement commonly known as a Bowden cable.

The steering wire running along the inside of the guide tube in a Bowden cable arrangement normally extends with a predetermined length over either end, allowing an operating member to be attached to a free (proximal) end of the wire, and an operated member to be attached to the other free (distal) end. When the ends of the guide tube are held stationary, movement of the proximal end of the steering wire with respect to the guide tube is transmitted to the distal end as a corresponding movement of the distal end of the steering wire with respect to the guide tube, so as to affect a movement of the operated member. The fastening of the proximal end of the guide tube to the operating handle is generally achieved with mechanical means where the guide tube is clamped, terminated in a block member, or adhered to the operating handle.

In order for the operator to have a good and responsive experience controlling the endoscope, the steering wire is maintained in a pre-tensioned state. If the maintained tension of the steering wire is too high, the steerable tip may be non-straight or mechanical parts of the endoscope may break. On the other hand, if the tension of the steering wire is too low, the steering wire will have too much play during articulation of the steerable tip and may be unresponsive to the control of the operator. Therefore, the tension of the steering wire is adjusted before fixation of the steering wire, and the tension is maintained.

In a known method of attaching a steering wire to a control element in an endoscope, a steel control wire is threaded through holes in the control element, tensioned, and then crimped to itself. The control element, in the form of a disk roller, is movable in relation to the operating handle. The steering wire is inserted through a crimping member, then it is inserted through a first hole of the control element, then it is positioned around a bend of the control element and inserted through a different, second, hole of the control element, which extends in parallel to the first hole, and then the steering wire is inserted through the same crimping member so that the steering wire forms a loop. The steering wire is then pulled to adjust the tension of the wire and the crimping member is clamped by a tool so as to form a crimp to fixate the steering wire to itself and maintain the tension of the steering wire.

This prior art method of attaching a steering wire in an endoscope requires precise handling of the steering wire, e.g. in order to insert the steering wire through the crimping member and the holes of the control element. This process can be prone to errors and may be time-consuming. Furthermore, precise handling of the steering wire during assembly may be difficult to automate. Furthermore, it may be difficult to correctly adjust the tension of the steering wire.

It is generally desired that the fixation of the steering wire is resistant to aging, for instance during transport. This is especially desired for disposable endoscopes so as to not unduly limit the shelf life of the disposable endoscope.

On this background, it is an object of the present invention to provide an improved endoscope, preferably a disposable endoscope. Another object of the present invention is to provide an improved method for fixation of a wire portion of an endoscope.

SUMMARY

It is an object of the present disclosure to provide an improved endoscope, preferably a disposable endoscope, and an improved method for fixation of a wire portion of an endoscope. In some embodiments, a method for fixation of a wire portion of an endoscope is provided, the method comprising: a) providing: an operating handle; an insertion tube with a proximal end and a distal end, and with a steerable tip part located at the distal end; a control element movable in relation to the operating handle, the control element having at least one wall, a rotation axis, a lever extending from the rotation axis through a shell of the operating handle, a control member connected to the lever and operable to rotate the control element, and a pin spacing defined in the at least one wall of the control element; a pin comprising a wire guide; and a steering wire having a first wire portion connected to the steerable tip part, a second wire portion, and a third wire portion, the second wire portion being located between the first and third wire portions; b) pulling the third wire portion so as to tension the steering wire; and c) inserting the pin into the pin spacing so that the second wire portion is positioned in the wire guide and is clamped between the pin and the at least one wall of the control element, whereby the pin and the second wire portion are fixated to the control element so as to maintain a wire tension between the first and second wire portions.

In some embodiments, an endoscope is provided, the endoscope comprising: an operating handle; an insertion tube with a proximal end and a distal end, and with a steerable tip part located at the distal end; a control element movable in relation to the operating handle, the control element having a pin spacing defined by at least one wall of the control element; at least one tensioned steering wire having a first wire portion connected to the steerable tip part and a second wire portion connected to the control element, the steering wire being tensioned between the first and second wire portions; and a pin located in the pin spacing, the pin comprising a wire guide and a portion of the wire being located in the wire guide, wherein the second wire portion is connected to the control element by being clamped between the pin and the at least one wall of the control element so that the second wire portion is fixated in relation to the control element.

BRIEF DESCRIPTION OF THE DRAWINGS

Embodiments of the present disclosure will now be described, by way of example only, with reference to the accompanying drawings, in which:

FIG. 7c is a view similar to that of FIG. 7b of the pin according to FIG. 7b after insertion into the pin spacing in a final position.

DETAILED DESCRIPTION

Figure 1:
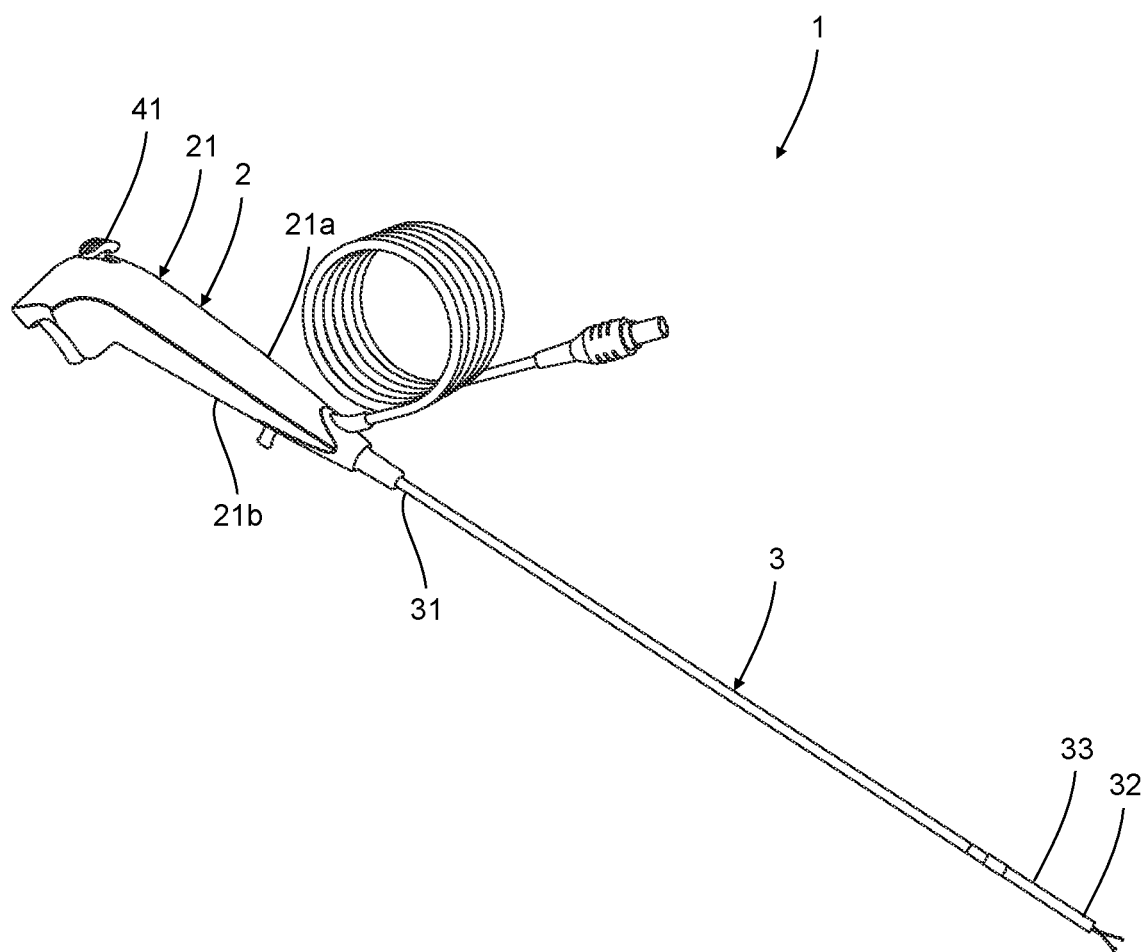
FIG. 1 is a perspective view of an endoscope.

The embodiments described below are merely exemplary and are not intended to limit the disclosure to the precise forms disclosed. Instead, the embodiments were selected for description to enable one of ordinary skill in the art to practice the disclosure.

The term "endoscope" as used herein is a device suitable for examination of spaces, including natural and/or artificial body openings, e.g. for exploration of a lung cavity. An endoscope may be a medical device. Examples of endoscopes include colonoscopes, bronchoscopes, gastroscopes, rhinolaryngoscopes and sigmoidoscopes, among other scopes. The insertion tube of the endoscope, or a distal end thereof, may be suitable for insertion into a body cavity, potentially a lung, through a body opening, potentially a mouth. The body may be a natural and/or artificial body, potentially a human body. The insertion tube may extend from the operating handle towards a distal end of the endoscope.

As used herein, the terms "distal" and "proximal" are relative to an operator of the endoscope, proximal being the end closest to the operator and distal being the end remote from the operator.

The term "steering wire" may be defined as an elongate member suitable for the purpose of controlling a steerable tip part by means of a control element, potentially as forming part of a cord drive or a Bowden cable arrangement for this purpose. The steering wire may further be tensionable. The term "steering wire" may include one or more from the group consisting of: a line, a cord, a thread, a string, a rope, a wire rope, a stranded wire rope, a cable, and a fishing line. Additionally or alternatively, the steering wire may be a monostranded, monofilament, multistranded or multifilament wire. A multistranded wire may also be known as a wire rope. In case of a multistranded wire, the strands may be braided, twisted, woven, coiled, or coiled wound.

The term "partly enclosing" may alternatively be denoted as partly surrounding or partly covering.

A first aspect of the invention relates to a method for fixation of a wire portion of an endoscope. A second aspect of the invention relates to an endoscope made by the foregoing method. In one embodiment, a method according to the first aspect comprises a) providing: an operating handle; an insertion tube with a proximal end and a distal end, and with a steerable tip part located at the distal end; a control element movable in relation to the operating handle, the control element having a pin spacing defined by at least one wall of the control element; a pin; and a steering wire having a first wire portion connected to the steerable tip part, a second wire portion, and a third wire portion, the second wire portion being located between the first and third wire portions; b) pulling the third wire portion so as to tension the steering wire; and c) inserting the pin into the pin spacing so that the second wire portion is clamped between the pin and the at least one wall of the control element. Clamping fixates the pin and the second wire portion to the control element so as to maintain the steering wire tension between the first and second wire portions. As used in the present embodiment, steps a) b) and c) may be performed by employees, agents, or members (i.e. workers) of an organization at the direction of a supervisor of the organization. For example, "providing" may comprise one worker giving the recited parts to another worker to perform steps b) and c). The worker providing the parts may have obtained the parts from a manufacturing machine or purchased them.

Advantageously, inserting the pin to fixate the steering wire simplifies assembly and may reduce the need for precise handling of the steering wire. This may, in turn, reduce the amount of labour required to perform the method, which may reduce the cost and time required to assemble the endoscope. A reduction in the amount of labour may allow the method to more easily be automated. It has further been shown that an endoscope manufactured according to this method can be provided so at to be resistant to aging, i.e. the tension can, to a higher degree, be maintained during the shelf life of the endoscope.

The method according to the first aspect of the invention may alternatively be provided as a method for fixation of a wire portion in a set of parts for an endoscope, the method comprising the steps a) to c) above.

The method according to the first aspect of the invention may alternatively be provided as a method for fixation of a wire portion in a set of parts for an endoscope, the method comprising the steps a) to c) above.

The steering wire may comprise or essentially consist of one or more materials selected from the group consisting of: metal, steel, polymer, plastic, polyethylene (PE), polyimide (PA), polyamide-imides (PAI), ultra-high-molecular-weight polyethylene (UHMWPE), high-density polyethylene (HDPE), low-density polyethylene (LDPE), high-molecular-weight polyethylene (HMWPE), natural fibres, artificial fibres, glass fibres, and carbon fibres. The steering wire may be less than 1 mm in diameter, less than 0.75 mm in diameter, less than 0.60 mm in diameter, less than 0.40 mm in diameter, or less than 0.30 mm in diameter.

The second and third wire portions of the steering wire may be coinciding or the same wire portion. Alternatively, the second and third wire portions of the steering wire may be located at a distance from each other.

During step b) of the method according to the first aspect of the invention, the wire may be tensioned to a first wire tension, and/or during step c), the tension of the wire may be maintained at a second wire tension. The first wire tension may be substantially the same as the second wire tension. Alternatively, the first and second wire tensions are different from each other.

The steps of the method according to the first aspect of the invention may be performed sequentially, potentially in the order a), b), c) or in the order a), c), b). Alternatively, or additionally, step a) may be performed during step b) and/or step c). The method may comprise the further step of releasing the third wire portion, which step may potentially be performed after step c) or after steps a), b) and c) have been performed.

In the endoscope assembled by the present embodiment of the method, the control element may be configured to allow an operator to control the steerable tip part of the insertion tube by the at least one steering wire. The control element may allow bending the steerable tip part in at least one direction, potentially in two directions, the two directions potentially being opposite. The control element may be accommodated in the operating handle. The control element may include a lever allowing an operator to control the control element. The lever may extend outwardly from the control element, potentially through the operating handle. The control element may be in the form of a roller or a roller disc.

The operating handle may be suitable for allowing an operator to grip and to operate the endoscope, potentially with one hand. The operating handle may comprise a handle housing arranged at a proximal end of the insertion tube. The handle housing may accommodate the control element.

The insertion tube or a distal end thereof may be suitable for insertion into a body cavity, potentially a lung, through a body opening, potentially a mouth. The body may be a natural and/or artificial body, potentially a human body. The insertion tube may extend from the operating handle towards a distal end of the endoscope.

The pin may be elongated and may be suitable for being fixated by insertion thereof into a pin spacing. This insertion may be manual or automated. The pin may further comprise a body and/or a head. The head may include a surface adapted to be pushed or hit, potentially so as to insert the pin into the pin spacing. The head may be located at a first end of the pin, and/or the pin snap part may be located at a second end of the pin.

The pin may be selected from the group consisting of: a split pin, a plug, a split plug, a dowel, a split dowel, a peg, a split peg, a rivet, a split rivet, an insert, and a split insert.

In some embodiments, step a) of the method according to the first aspect of the invention further comprises providing a wire support, in which the steering wire is guided, and which is potentially fixated to the operating handle, wherein in step b) the steering wire potentially extends along a first direction from an exit from the wire support, and wherein a pulling force exerted on the third wire portion potentially extends in a second direction, an angle between the first and second directions potentially being less than 120°. This angle between the first and second directions may be less than 110°, 100°, or 90°. This angle may be the smallest angle measured in a common plane of the two directions. This angle may be measured between the two directions extending from a common starting point. This angle may be defined so that, if the first and second directions are parallel and extend in opposite directions, the angle is 180°, if the first and second directions are perpendicular, the angle between them is 90°, and if the first and second directions are parallel and extend in the same direction, the angle between them is 0°.

The wire support may be a guide tube for guiding the steering wire, and/or the wire support may at least partly enclose, surround, and/or accommodate a portion of the steering wire. The wire support may extend between the steerable tip part and the operating handle. The insertion tube may at least partly enclose a portion of the wire support. The wire support may be attached to the operating handle.

The steering wire may first be pulled in the first direction, potentially by pulling the third wire portion, then bent around the wire support and then pulled in the second direction.

In some embodiments, the method according to the first aspect of the invention further comprises the step of:

d) applying an adhesive to the second wire portion, the pin spacing and/or on the pin.

Step d) may be performed prior to step c). Alternatively, step d) may be performed subsequent to step c). The adhesive may be applied as a liquid adhesive, and/or may be a reactive adhesive and/or a chemically curing adhesive, and/or may be converted from a liquid state to a solid state from a chemical reaction. The chemical reaction may be initiated by heat, moisture, radiation, and/or pressure. The adhesive may be a single component adhesive chosen from the group consisting of: anaerobic, cyanoacrylate, heat hardenable, moisture hardenable, radiation hardenable and silicone adhesive. The cyanoacrylate adhesive may be an ethyl 2-cyanoacrylate adhesive.

In some embodiments, one or both of the pin snap part and the associated snap part comprise(s) at least one resilient leg, potentially with a barb, wherein in step c), during insertion of the pin into the pin spacing, the resilient leg is optionally deflected from a resting position, and/or, after insertion of the pin into the pin spacing, the resilient leg returns towards the resting position so that the barb potentially snaps into engagement with the other of the pin snap part and the associated snap part.

The barb may be outwardly extending from the associated resilient leg. The pin snap part may comprise the at least one resilient leg. After insertion of the pin into the pin spacing, the resilient leg may return to the resting position.

The resilient leg may be an elongate member extending substantially along a length direction. A length of the resilient leg in the length direction may be more than 2 mm, more than 3 mm, more than 4 mm, more than 4.5 mm, or more than 5 mm. The length of the resilient leg may be less than 20 mm, less than 15 mm, less than 12 mm, less than 10 mm or less than 8 mm. The length of the resilient leg may be 2-20 mm, 3-15 mm, 4-12 mm, 4.5-10 mm or 5-8 mm.

In some embodiments of the method according to the first aspect of the invention, in step c) the pin deforms the second wire portion. This deformation may occur during insertion of the pin and/or before insertion of the pin. The deformation may comprise at least one bend of the wire, preferably at least two bends.

In some embodiments, the pin spacing is at least partly defined by a wall, and in step c) the second wire portion may furthermore be clamped between the pin and the wall. Hereby, the second wire portion may be fixated to the control element so as to maintain a wire tension between the first and second wire portions.

In some embodiments, the pin comprises a wire guide, and the method may further comprise the step of positioning of the second wire portion in the wire guide. This step may ensure a controlled handling of the second wire portion so as to ensure a good fixation of the second wire portion.

In some embodiments, the pin snap part comprises two resilient legs, each potentially having a barb, the resilient legs potentially being arranged at a distance from each other, and a wire guide potentially being located between the resilient legs. Hereby, the pin may be provided as a split pin, a split plug, a split dowel, a split peg, a split rivet, and/or a split insert, wherein a split is provided between the two legs. Prior to step c) of the method, the wire may be positioned in the wire guide. Additionally, or alternatively, the pin may be inserted so that the wire is positioned in the wire guide during step c) of the method. The two resilient legs may be provided so as to be substantially parallel to each other, especially in undeformed states thereof, and/or the barbs may be located on opposite sides of the legs. During insertion of the pin into the pin spacing in step c) of the method, the resilient legs are optionally deflected, potentially by the wall, from a resting position, and, after insertion of the pin into the pin spacing, the resilient legs may return towards the resting position so that the barbs potentially snap into engagement with the associated snap part, potentially one or more associated barbs of the latter.

In some embodiments, the pin spacing is at least partly defined by at least one wall, and in step c) the second wire portion is fixated by bending the second wire portion around at least one corner or edge of the pin and/or of the wall so as to potentially form at least one wire step. The second wire portion may be bent around at least two, three, four, five or more corners or edges of the pin and/or of the at least one wall. The at least one wall may comprise at least one of the corners, and the pin may comprise at least another one of the corners. Alternatively, or additionally, after step c) of the method according to the first aspect of the invention, the steering wire forms at least two wire steps, preferably at least three wire steps, more preferably at least four wire steps between a portion of the steering wire located before the pin spacing to a different portion located after the pin spacing. When the wire is bent around a corner or edge, the wire may form a wire step, in which the wire forms an angle of at least 30°, 45°, 60°, 70° or 80°.

In some embodiments, step a) further comprises providing a first wire guide, which is potentially fixated to the control element, the wire guide optionally being provided adjacent to the pin spacing, and wherein in step c) the steering wire is guided through the wire guide. Hereby, the wire may be bent around the wire guide so as to form a wire curve. The wire guide may comprise a bending channel with a rounded surface on which the wire abuts so that the bend is not an angle in geometric or mathematical terms, but rather provides a rounded wire portion (such a rounded portion of the wire may also fall within the term "angle" as used herein). This may improve reliance of the wire tensioning since it may alleviate a tendency of the steering wire to be at least partly stuck in the bend. The wire guide may at least partly envelop or surround a portion of the steering wire. This portion may be a bent portion. The wire guide may be provided with a mouth opening to the pin spacing. The first wire guide may be provided as a channel, a surface groove and/or a duct. The first wire guide may be provided for guiding a first wire, and a second wire guide may be provided for guiding a second wire. In this case, the first and second wire guides may be identical or mirrored versions of each other. The second wire guide may comprise one or more of the above options described for the first wire guide.

In some embodiments, the steering wire is a first steering wire, the pin is a first pin, and the pin spacing is a first pin spacing; and step a) further comprises: providing a second steering wire having a first wire portion connected to the steerable tip part, a second wire portion, and a third wire portion, the second wire portion being located between the first and third wire portions; optionally a second pin with a snap part; and optionally a second pin spacing with an associated second pin snap part; and the method may further comprise the step, optionally to be performed simultaneously with step b) of the method, of pulling the third wire portion of the second steering wire so as to tension the second steering wire; and the method may further comprise the step, optionally to be performed simultaneously with step c) of the method, of inserting the second pin into the second pin spacing so that the pin snap part snaps into engagement with the associated snap part, whereby the second pin and the second wire portion are optionally fixated to the control element potentially so as to maintain a wire tension between the first and second wire portions.

The second steering wire may be provided to be similar or identical to or being a mirrored version of the first steering wire. The second steering wire may be connected to the first steering wire, potentially at the first wire portions thereof. Alternatively, or additionally, the second steering wire may be connected to the first steering wire at the steerable tip part.

The first and second pins may be one and the same pin, i.e. be coinciding, or they may be different pins. The second pin may be provided to be similar or identical to the first pin, or they may be different. The first and second pin spacings may be one and the same pin spacing, i.e. they may be coinciding, or they may be different pin spacings. The second pin spacing may be provided to be similar or identical to the first pin spacing. The method steps relating to the second steering wire may include corresponding method steps as for the first steering wire and/or may include one or more of the options described above for the first steering wire.

In an endoscope assembled by the method according to the first aspect of the invention, the first steering wire may enable the control element to allow an operator to control the steerable tip part in a first direction, and/or the second steering wire may enable the control element to allow an operator to control the steerable tip part in a second, different direction. Alternatively, or additionally, the first steering wire may allow the control element to bend the steerable tip part in a first direction, and/or the second steering wire may allow the control element to bend the steerable tip part in a second direction. The second direction may be a direction opposite in relation to the first direction.

The control element may comprise a second wire guide for accommodating the second steering wire. The second wire guide may be provided in a similar way as the first wire guide and/or may comprise one or more of the options described above for the first wire guide.

In another embodiment, the pin comprises an arm, and, before or during step c), the pin is rotated by means of the arm to assume a rotated position, wherein the arm optionally maintains the pin in the rotated position when the pin is inserted into the pin spacing. The arm may extend laterally from a head and/or body of the pin and/or may be integral with the pin. The arm may extend in a radial direction normal to a longitudinal or length direction of the pin. The arm may extend to be substantially straight or curved in the lateral direction or have any other suitable shape. In case the pin further comprises a wire guide as described in the above, the second wire portion may be positioned the pin before the arm rotates the pin. The pin may then be at least partly introduced into the pin spacing, potentially so that the second wire portion is at least partly positioned in the pin spacing. The pin may before or after insertion of the pin into the pin spacing be rotated by means of the arm, whereby the second wire portion may be pulled to extend at least partly around the pin so that the part of the second wire portion that extends around the pin is clamped between the pin and the at least one wall when the pin assumes the rotated position. The pin may then potentially be inserted into a final, inserted position in the pin spacing, and the arm may be released. In this case, the control element may comprise an arm support, which may be in the form of a wall. A tension of the steering wire may then pull the arm in a direction opposite the direction in which the arm was rotated so that the steering wire tension pushes the arm against the arm support so as to prevent the arm from rotating further towards the arm's position before the rotation thereof. Hereby steering wire tension may be applied to fixate the pin in the pin spacing. Furthermore, a larger part of the steering wire second portion may be clamped between the pin and the at least one wall of the control element, which may provide a stronger fixation of the steering wire.

The present embodiment may be combined with one of the above embodiments in which the pin comprises a snap part. After the arm is rotated, when the pin is pushed into the final, inserted position, the pin snap part may snap into the associated snap part of the control element. Hereby, fixation of the pin in the pin spacing may be further improved. Alternatively, or additionally, a snap part may be included in the arm, which in a manner similar to the above described snap part of the pin may snap into an associated snap part of the control element.

The second aspect of the invention relates to an endoscope. In one embodiment, the endoscope comprises: an operating handle; an insertion tube with a proximal end and a distal end, and with a steerable tip part located at the distal end; a control element movable in relation to the operating handle, the control element having a pin spacing defined by at least one wall of the control element; at least one tensioned steering wire having a first wire portion connected to the steerable tip part, and a second wire portion connected to the control element, the steering wire being tensioned between the first and second wire portions; and a pin located in the pin spacing; wherein the second wire portion is connected to the control element by being clamped between the pin and the at least one wall of the control element so that the second wire portion is fixated in relation to the control element.

The endoscope of the present embodiment may be manufactured by means of one or more of the above embodiments of the method according to first aspect of the invention.

The endoscope may alternatively be provided as a set of parts for an endoscope, the set of parts comprising: an operating handle; an insertion tube with a proximal end and a distal end, and with a steerable tip part located at the distal end; a control element movable in relation to the operating handle, the control element having a pin spacing defined by at least one wall of the control element; at least one tensioned steering wire having a first wire portion connected to the steerable tip part, and a second wire portion connected to the control element, the steering wire being tensioned between the first and second wire portions; and a pin located in the pin spacing; wherein the second wire portion is connected to the control element by being clamped between the pin and the at least one wall of the control element so that the second wire portion is fixated in relation to the control element.

In some variations of the present embodiment, the pin spacing is at least partly defined by at least one wall. The control element may comprise the at least one wall. The pin spacing may be defined by two opposite walls. The pin spacing may be a hole and/or a cavity. The pin spacing may be substantially cylindrical and/or rectangular in cross section.

In some variations of the present embodiment, the pin comprises a wire guide, and the steering wire may be located in the wire guide. The wire guide of the pin may be a hole through the pin, a potentially elongated recess in the pin, a channel in the pin, or a channel extending on a surface of the pin. The wire guide may extend through the pin and/or may be provided to extend along an outer edge or outer surface of the pin, wherein a steering wire channel may be defined between surfaces of the pin and/or a surface of a wall of the control element or the pin spacing.

In some embodiments, the pin and/or the at least one wall comprises at least one corner or edge, and the second wire portion may be bent around the at least one corner or edge so as to potentially form at least one wire step. The second wire portion may be bent around at least two, three, four or more corners or edges of the pin and/or the at least one wall. The at least one wall may comprise at least one of the corners, and the pin may comprise at least another one of the corners. At the location of the bend of the wire, the wire may form a wire step, in which the wire forms an angle of at least 30°, 45°, 60°, 70° or 80°.

Alternatively, or additionally, the pin comprises a first set of pin corners with at least one pin corner, and the at least one wall comprises a first set of wall corners with at least one wall corner, wherein the second wire portion is bent around the first sets of corners.

In some embodiments, the steering wire is a first steering wire, and the pin is a first pin, the pin spacing is a first pin spacing, and the control element further has a second pin spacing defined by at least one wall of the control element, the endoscope further comprising:

a second tensioned steering wire having a first wire portion connected to the steerable tip part, and a second wire portion connected to the control element, the steering wire being tensioned between the first and second wire portions; and a second pin located in the second pin spacing;

wherein the second wire portion of the second steering wire is connected to the control element by being clamped between the second pin and the at least one wall of the control element so that the second wire portion is fixated in relation to the control element.

The second steering wire may be provided to be similar or identical to the first steering wire. The second steering wire may be connected to the first steering wire, potentially at the first wire portions thereof. Alternatively, or additionally, the second steering wire may be connected to the first steering wire at the steerable tip part. The first and second pins may be one and the same pin, i.e. may be coinciding, or they may be different pins. The second pin may be provided similarly to the first pin or they may be different. The first and second pin spacing may be the same pin spacing or they may be different pin spacings. The second pin spacing may be provided similarly to the first pin spacing.

Any one or more of the embodiments relating to the first or second aspect of the invention may be combined with any one or more of the embodiments relating to either the same aspect of a different aspect.

Referring not to the figures, FIG. 1 shows an endoscope 1 according to an embodiment of the second aspect of the invention assembled by a method according to an embodiment of the second aspect of the invention. The endoscope 1 comprises an operating handle 2, an insertion tube 3, and a control element 4, see also FIG. 2. The operating handle 2 is a handle suitable for allowing an operator to grip and to operate the endoscope 1 with one hand. A handle housing 21, comprising two shells 21a, 21b, accommodates the control element 4.

The insertion tube 3 is an elongate member suitable for insertion into a patient, such as into a patient's lung through the patient's mouth. The insertion tube 3 extends from the operating handle 2 towards a distal end (to the right in FIG. 1) of the endoscope 1. The insertion tube 3 has a proximal end 31 connected to the handle housing and a distal end 32, and with a steerable tip part 33 located at the distal end 32.

Figure 2:
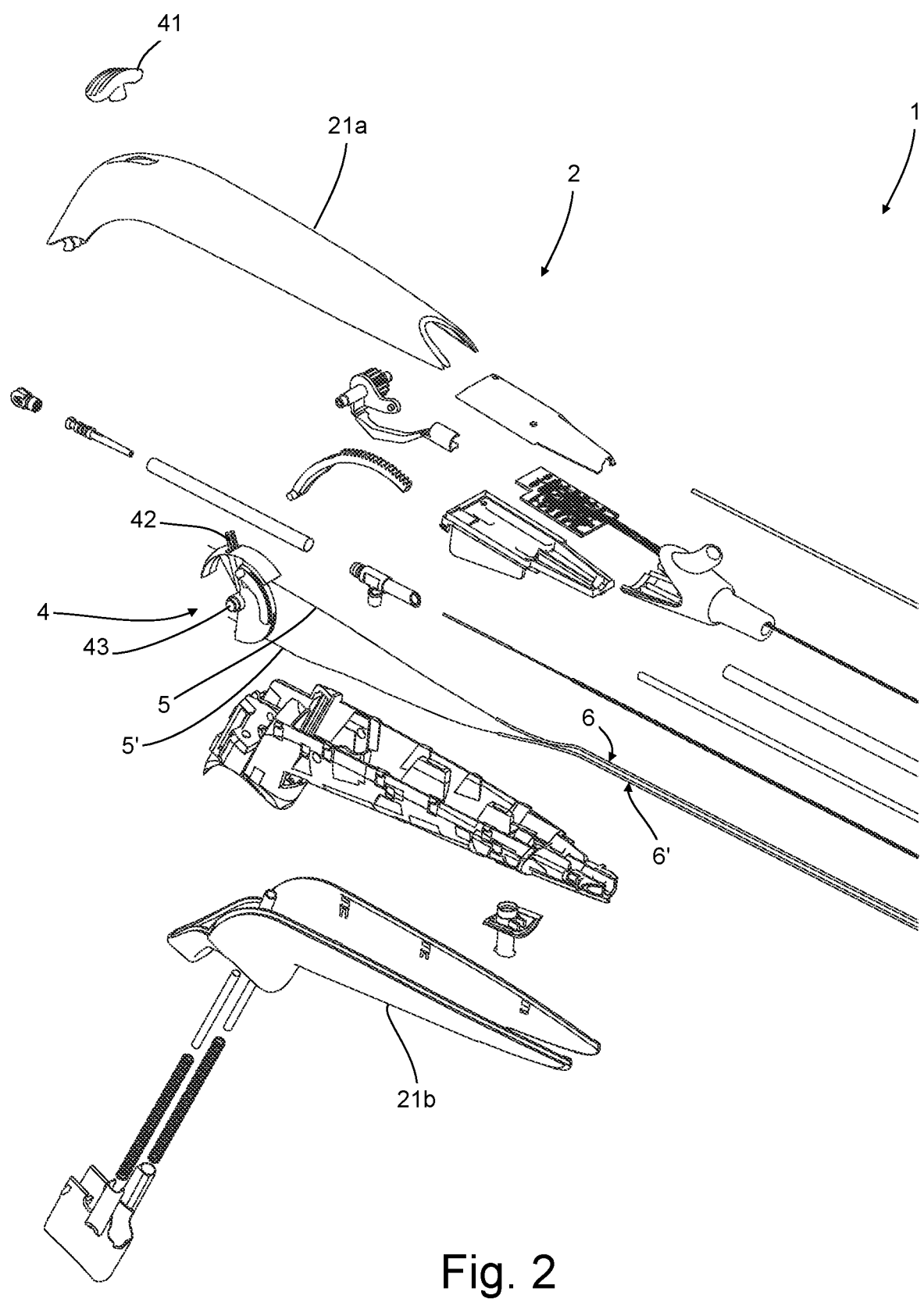
FIG. 2 is an exploded perspective view of the endoscope of FIG. 1.

The control element 4 is configured to allow an operator to control the steerable tip part 33 of the insertion tube 3 by two steering wires 5, 5', see also FIG. 2. The control element 4 allows bending the steerable tip part 33 in two directions. The control element 4 includes an operating member 41 allowing an operator to control the control element 4. The operating member 41 is connected to a lever 42 connected to and extending outwardly from a rotating axis 43 of the control element 4 through the handle housing 21 and is movable in relation to the operating handle 2. The lever 42 allows an operator to rotate the control element 4 around an axis 43 in a known manner.

FIG. 2 shows an exploded view of the parts of the endoscope 1 of FIG. 1. The endoscope 1 comprises the first 5 and second 5' steering wires, respectively located in a first 6 and a second 6' wire support in the form of a respective first and a second guide tube in which the steering wires 5, 5' are respectively slidable. The apostrophe suffix of a reference number as used herein generally denotes an element associated with the second steering wire 5' corresponding to a similar element associated with the first steering wire 5, so that the first wire support 6 is associated with the first steering wire 5, and the second wire support 6' is associated with the second steering wire 5'. In the following, features are described primarily in relation to the first steering wire 5; however, similar features relating to the second steering wire 5' are also provided in the endoscope 1 as shown in the drawings.

Each steering wire 5, 5' is an elongated wire forming part of a Bowden cable arrangement controlling the steerable tip part 33 by means of the control element 4. Each steering wire 5, 5' consists essentially of a steel wire rope. Each steering wire 5, 5' has a diameter of about 0.25 mm.

Figure 4:
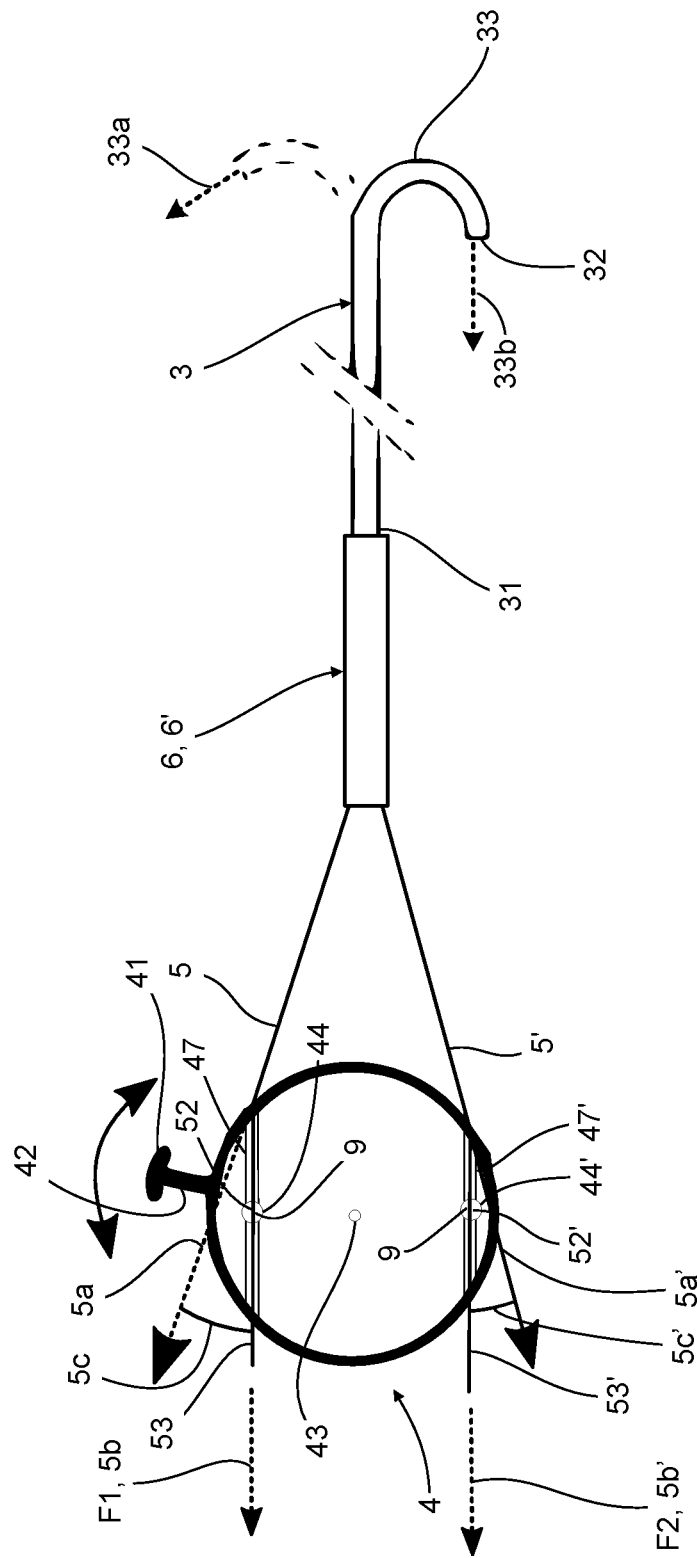
FIG. 4 is a side view schematically illustrating operation of a steerable tip of an endoscope and associated tensioning of steering wires.

Referring also to FIG. 4, each steering wire 5, 5' has a respective first (not shown), second 52, 52' and third 53, 53' wire portion. Each of the first wire portions is connected to the steerable tip part 33. The wire portions are spaced from each other and located in sequence first to third along each steering wire 5, 5' so that going from the first wire portion along the respective steering wire 5, 5', the next wire portion is the second wire portion 52, 52', and lastly the third wire portion 53, 53' which terminates in a wire end.

To fixate the second wire portions 52, 52' to the control element 4, a pin 9 is inserted into the pin spacing 44, 44' so as to maintain a wire tension between the first and second 52, 52' wire portions.

Figure 3:
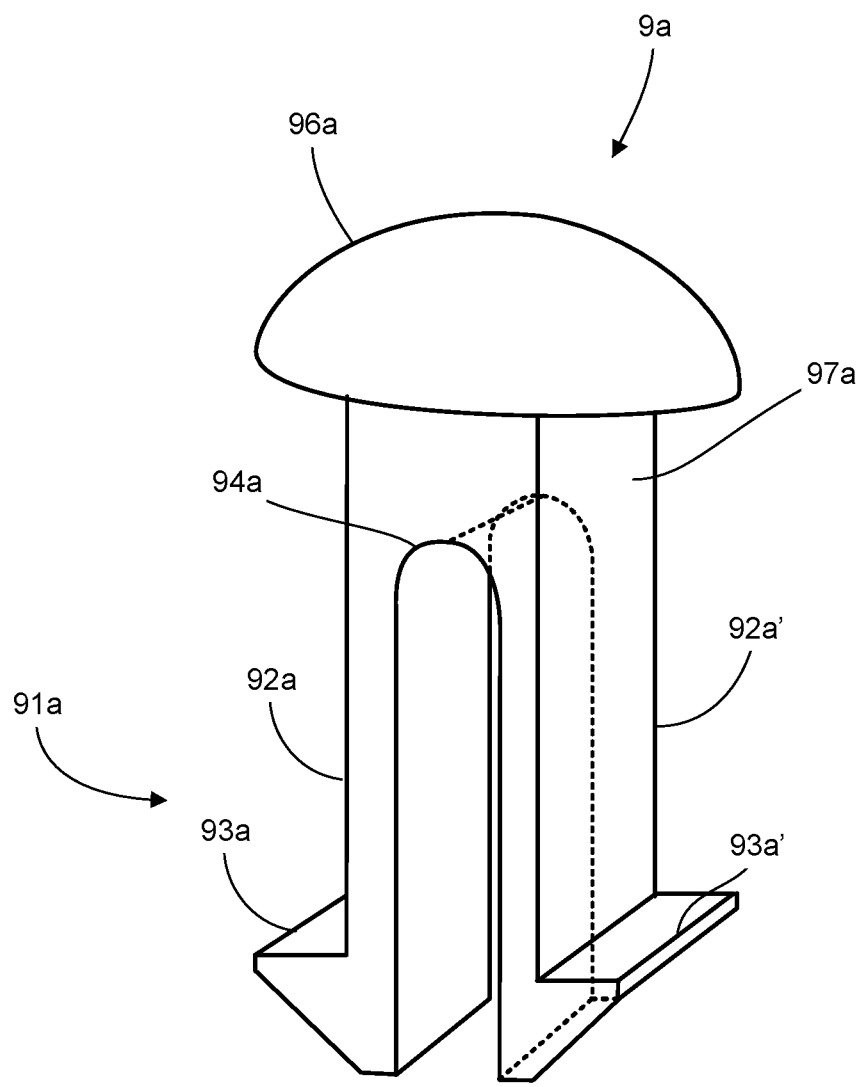
FIG. 3 is a perspective view of a first embodiment of a pin.

FIG. 3 shows a first embodiment, denoted 9a, of the pin 9. The pin 9a is an elongated member fixated by insertion into a pin spacing 44, see FIG. 4. The pin 9a has a snap part 91a, a wire guide 94a, a head 96a, and a body 97a. The head 96a is located at a first end of the pin 9a, and the pin snap part 91a is located at a second end of the pin 9a, the body 97a being located between the snap part 91a and the head 96a. The head 96a is mushroom shaped and includes a top surface adapted to be pushed or hit in order to push the pin 9a into the pin spacing 44, 44'. The pin snap part 91a comprises two parallel resilient legs 92a, 92a', each having a barb 93a, 93a' located at opposite sides of the legs 92a, 92a'. Each barb 93a, 93a' extends outwardly from the associated resilient leg 92a, 92a'. Hereby, the pin 9a is provided as a split pin, wherein the split is provided between the two legs 92a, 92a'. The resilient legs 92a, 92a' are arranged at a distance from each other, and a wire guide 94a is located between the resilient legs 92a, 92a'. Each barb 93a, 93a' comprises an outwardly extending projection with a top surface extending substantially perpendicularly to the length direction of the pin 9a and an inclined bottom surface. The wire guide 94a extends through the pin and is defined by a rounded surface at a top and is open at a bottom, an opening of the wire guide 94a opening into the split. A length of each of the resilient legs 92a, 92a' is approximately 6 mm. The resilient legs are identical and oppositely positioned to each other.

Figure 5A:
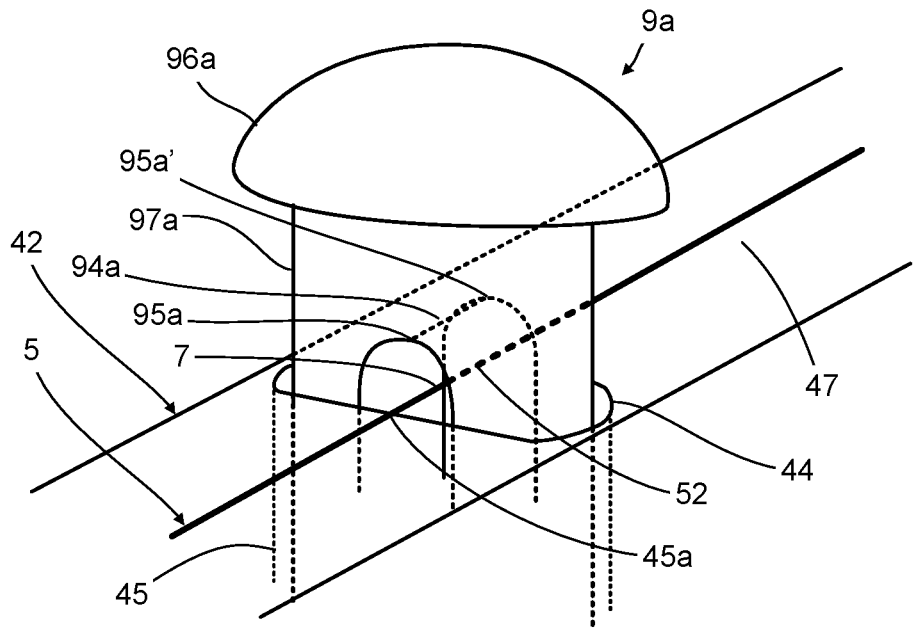
FIG. 5a perspective view of the pin of FIG. 3 prior to insertion into a pin spacing, with hidden lines shown as dashed lines.
Figure 5B:
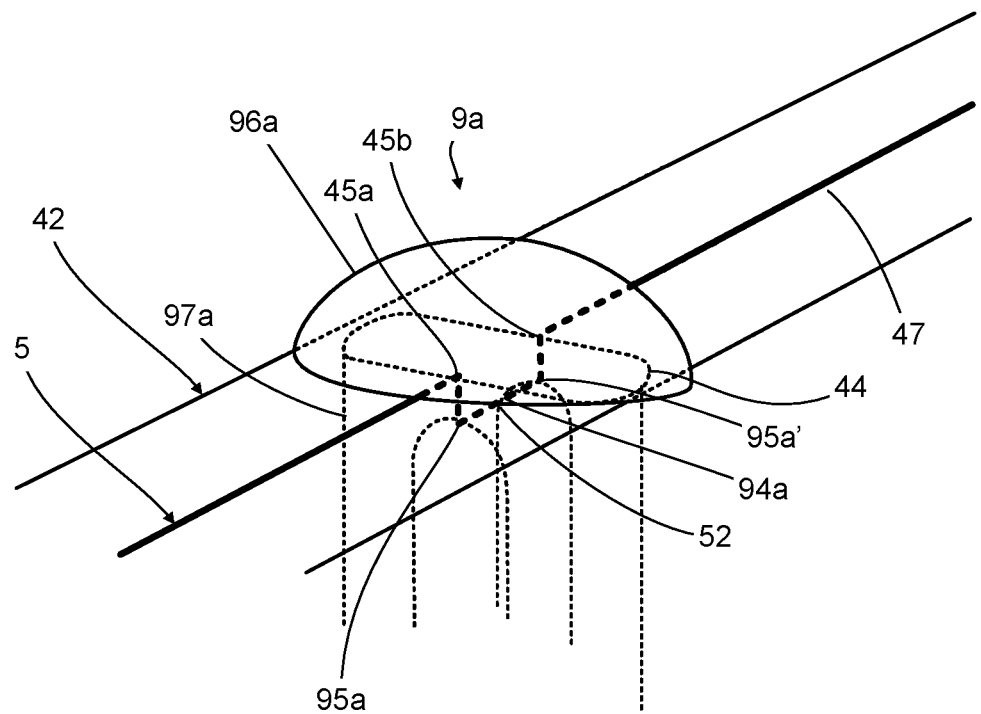
FIG. 5b is a view similar to that of FIG. 5a of the pin according to FIG. 5a shown after insertion into the pin spacing.

FIGS. 4, 5a, and 5b schematically show an embodiment of the method according to the first aspect of the invention for attaching the two steering wires 5, 5' in the endoscope 1 so to allow control of the steerable tip part 33 by activation of the control element 4. The method can be provided in a similar fashion for an attaching a single steering wire. The guide tubes 6, 6' are schematically shown in FIG. 4 as a single guide tube 6, 6' which includes the two separate guide tubes 6, 6' as shown in FIG. 2.

Referring to FIG. 4, the method of attaching two steering wires 5, 5' is carried out as follows:

First, the control element 4 is provided. The control element 4 including two wire guides 47, 47' formed as surface channels on the control element 4: a first wire guide 47 for accommodating and partly enclosing a portion of the first steering wire 5, and a second wire guide 47' for accommodating and partly enclosing a portion of the second steering wire 5'. The wire guides 47, 47' are formed as recesses in a surface of the control element 4 and are each provided with two mouths, respectively opening to opposite sides of the pin spacing 44, 44'. The pin spacing 44, 44' is a substantially cylindrical hole in the control element 4. The pin spacing 44, 44' may generally have any suitable shape in cross section, such as round, circular, rectangular, ellipsoid etc.

Referring to FIG. 4, the first wire portion of the first steering wire 5 is attached to the steerable tip part 33 through the guide tube 6 so that, when pulled, the steerable tip part 33 bends in a first direction 33a, which is shown in dashed lines in FIG. 4. The first wire portion of the second steering wire 5' is attached to the steerable tip part 33 through the guide tube 6' so that, when pulled, the steerable tip part 33 bends in a second direction 33b, which is shown in solid lines in FIG. 4.

Second, each steering wire 5, 5' extends out from a proximal end of the respective guide tube 6, 6' in the operating handle 2 along a first direction 5a, 5a' and is positioned in the respective wire guide 47, 47' of the control element 4 so that the wire is bent in the respective wire guide 47, 47' so as to form a wire curve, and so that the second wire portion 52, 52' extends across a pin spacing 44, 44' of the control element 4. The steering wires 5, 5' are then bent to extend along a second direction 5b, 5b', and they then terminate at the third wire portion 53, 53' located at a wire end of the steering wire 5, 5'. The wire guides 47, 47' each comprises a bending channel with a rounded surface at an entry into the wire guides 47, 47' onto which the wire 5, 5' abuts so that the wire bends here are not at a geometric or mathematical angle, but rather provide a rounded wire portion. A respective angle 5c, 5c' between the respective first 5a, 5a' and second directions 5b, 5b' is 20° to 40°. This angle is the smallest angle measured in a common plane of the two directions and is measured between the directions extending from a common starting point.

Third, the third wire portions 53, 53' are each pulled with a force, denoted F1, F2, respectively, which is exerted in parallel to and coinciding with the second direction of the respective steering wires 5, 5' so as to tension the steering wires 5, 5' to a first wire tension between the first and the third 54, 54' wire portions. The tension of each wire 5, 5' is adjusted to a desired tension and so that the steerable tip part 33 is straight.

Fourth, as shown in FIG. 5a, a liquid adhesive 7 is optionally applied to an area of the second wire portion 52 prior to insertion of the pin 9a into the pin spacing 44. The adhesive 7 is a cyanoacrylate adhesive.

Fifth, referring to FIGS. 5a and 5b, the second wire portion 52 is positioned in the pin wire guide 94, and the pin 9a is inserted into the pin spacing 44 so that the pin snap part 91a snaps into engagement with an associated snap part of a wall 45 of the pin spacing 44, whereby the pin 9a and the second wire portion 52 are fixated to the control element 4 so as to maintain a wire tension between the first and second 52 wire portions by clamping the second wire portion 52 between a wall 45 of the pin spacing and the pin 9a. The wall 45 defines the pin spacing 44 by extending in an entire circumference of the pin 9a and has a cross-sectional shape similar to that of the pin body 97a. The associated snap part is not shown in FIGS. 5a and 5b, but is similar to the associated snap parts 48, 48' as shown in the pin embodiments of FIGS. 6a to 6d described below. The second wire portion 52 is fixated by bending the second wire portion around a first corner or edge 45a of the wall 45 and then a first corner 95a of the pin 9a so as to form a first wire step. The second wire portion 52 then continues along the pin wire guide 94a, until the second wire portion 52 is similarly bent around a second pin corner 95a' and a second wall corner 45b so as to form a second wire step. Each corner 45a, 45b, 95a, 95a' forms a substantially 90° bend of the second wire portion 52. Hereby, the second wire portion 52 is fixated by being clamped between the pin 9a and the wall 45 of the pin spacing 44 and by the first and second wire steps.

During insertion of the pin 9a into the pin spacing 44, the resilient legs 92a, 92a' are deflected via the inclined bottom surfaces of the respective barbs 93a, 93a' from their resting positions towards a centre of the pin spacing 44, and, after insertion of the pin 9a into the pin spacing 44, the resilient legs 92a snap to return to the resting position so that the barbs 93a, 93a' snap into engagement with the associated snap part to reach a fixated position similar to those shown in FIGS. 6a to 6d. Subsequently, the second wire portion 52 is clamped between the pin 9 and is also held in its fixated position by the described wire steps.

Figure 6A:
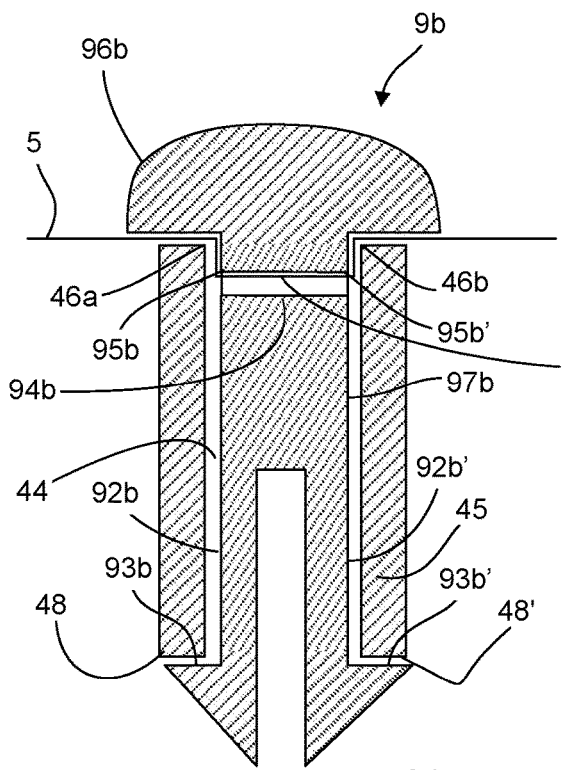
FIG. 6a is a cross-sectional side view of a second embodiment of a pin positioned in a pin spacing.
Figure 6B:
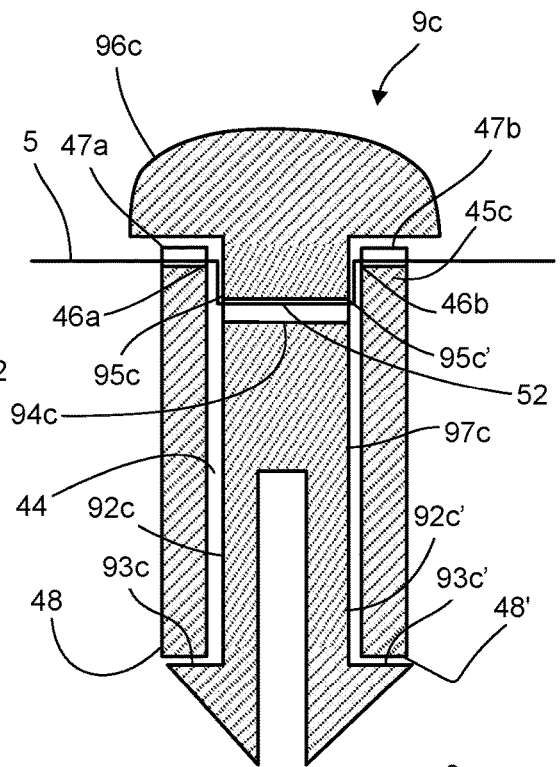
FIG. 6b is a view similar to that of FIG. 6a of a third embodiment of a pin positioned in a pin spacing.
Figure 6C:
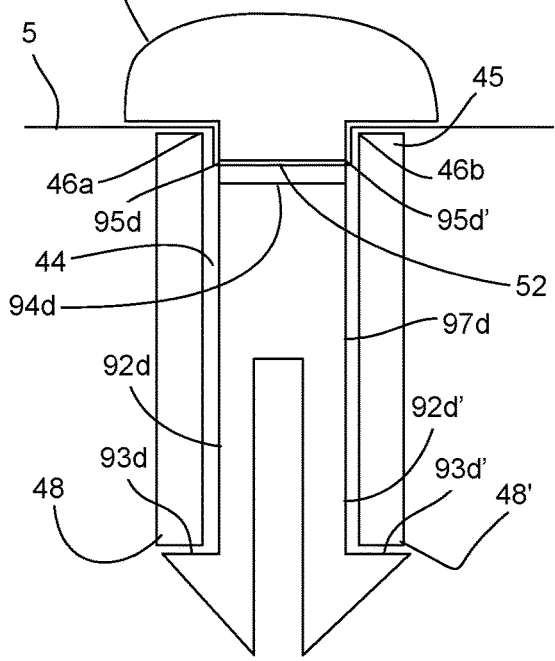
FIG. 6c is a view similar to that of FIG. 6a of a fourth embodiment of a pin positioned in a pin spacing.

FIGS. 6a to 6d show alternative embodiments of the pin 9, denoted 9b to 9e, respectively, and the pin wall 45. In the embodiments of FIGS. 6a and 6c, the wall 45 is identical to that of FIGS. 5a and 5b. Elements of FIGS. 6a to 6d similar or identical to respective elements of FIGS. 5a and 5b are denoted with identical reference signs, except so that the "a" of the reference signs of FIGS. 5a and 5b is replaced by the letter of the respective embodiment of the pin 9b, 9c, 9d and 9e.

FIG. 6a shows a second embodiment of the pin 9, denoted 9b. In this embodiment, the wire guide 94b is provided as a linear through-hole or bore extending directly through the pin 9b. The pin 9b is thus identical to the pin 9a, except for wire guide 94b being closed towards the split of the pin 9b.

FIG. 6b shows another embodiment of the wall 45, denoted 45c. The pin 9c is identical to the pin 9b. This embodiment differs from the previous embodiments in that the wall 45c has been modified to comprise a wire guide 47a provided as a surface channel on a top left part the wall 45c, and a wire guide 47b continues similarly on a top right part of the wall 45c. The wire 5 is positioned in the wire guides 47a, 47b.

FIG. 6c shows another embodiment of the pin 9, denoted 9d, which is a modified version of the pin 9b. In the pin 9d, the wire guide 94d is provided as a recess extending around a circumference of the body of the pin 9b.

Figure 6D:
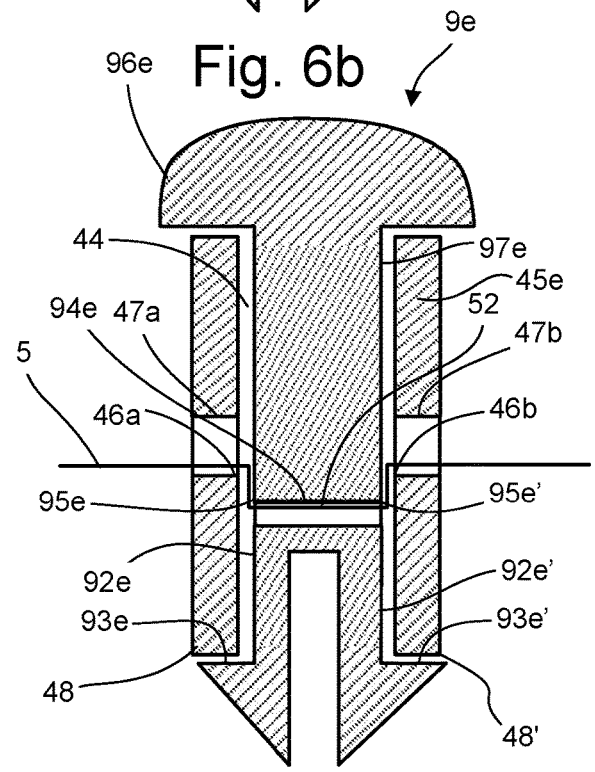
FIG. 6d is a view similar to that of FIG. 6a of a fifth embodiment of a pin positioned in a pin spacing.

FIG. 6d shows a fifth embodiment of the pin 9, denoted 9e, and the wall 45, denoted 45d. This embodiment is a modified version of that shown in FIG. 6b. The pin 9e differs from the pin 9c of FIG. 6b in that the wire guide 94e is positioned closer to the split so that the body 97e of the pin 9e is extended compared to that of the pin 9c. Furthermore, the wall 45c has been modified by including the wire guide 47b of the wall 45e at a lower position in the wall 45e so that it is provided as respective, opposite through-holes extending through the wall 45e.

In the embodiments of FIGS. 6a to 6d, the second wire portion 52 is fixated in a manner similar to as described in connection with the embodiment of FIGS. 5a and 5b.

Figure 7A:
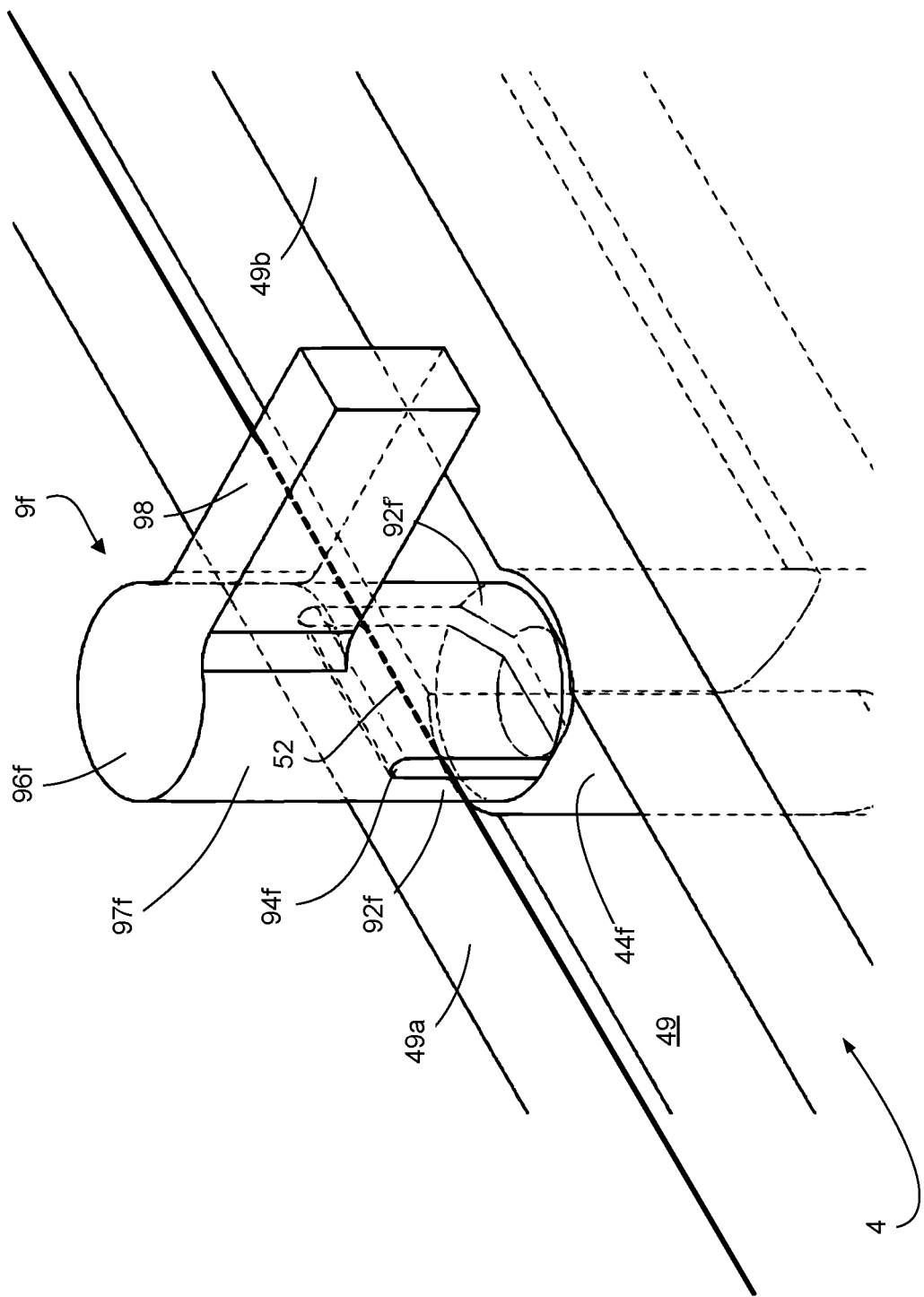
FIG. 7a is a perspective view similar to that of FIG. 5a of a sixth embodiment of a pin prior to insertion into a pin spacing, with hidden lines shown as dashed lines.
Figure 7B:
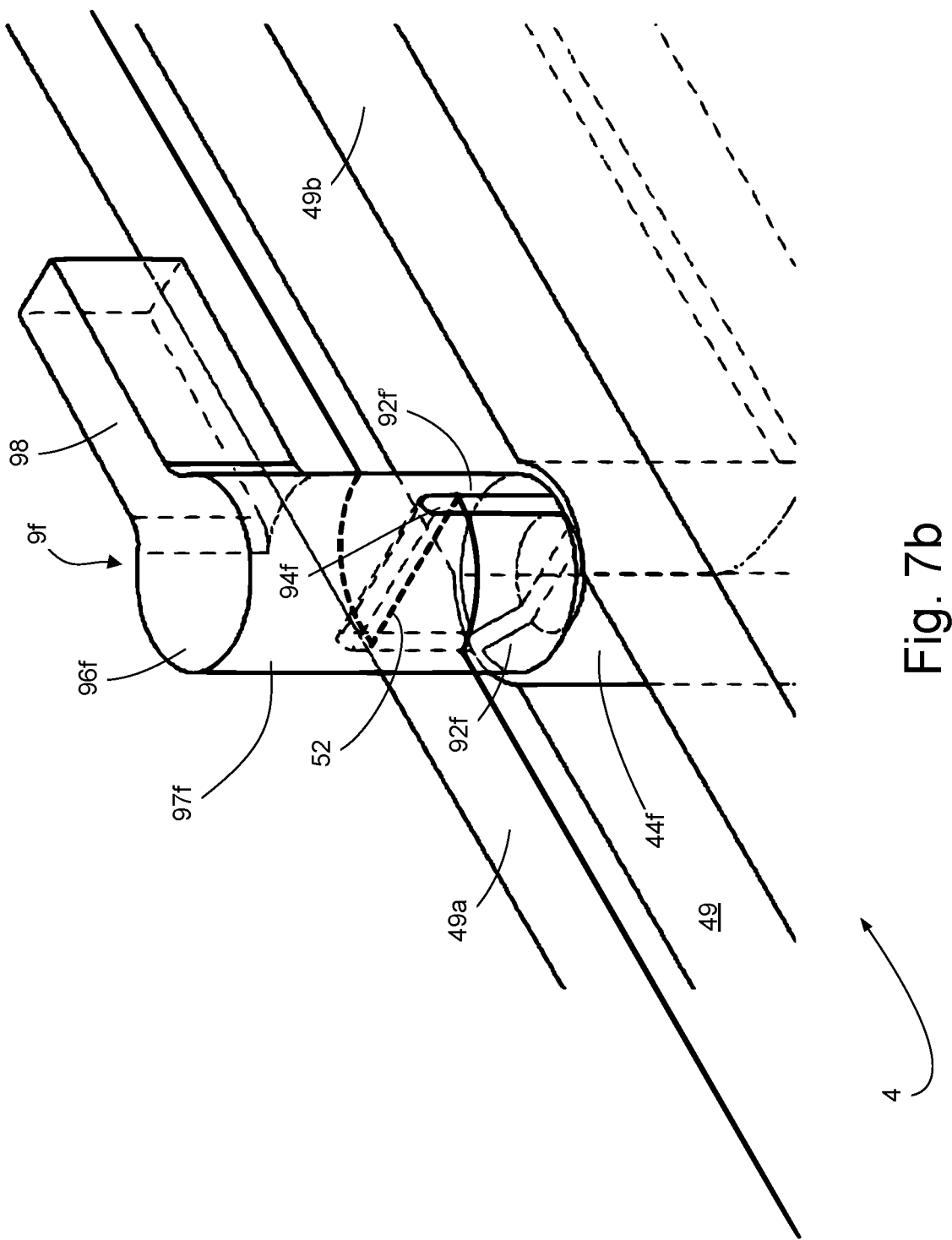
FIG. 7b is a view similar to that of FIG. 7a of the pin according to FIG. 7a prior to insertion into the pin spacing.

FIGS. 7a to 7c illustrate insertion of a sixth embodiment of the pin 9, denoted 9f, into a pin spacing 44f. The pin 9f is a modified version of the pin 9a especially in that it has no pin snap part at a second end and no head at a first end. The pin 9f may, however, comprise these parts as described further below. The pin 9f includes a wire guide 94f and a body 97f. A top surface 96f is adapted to be pushed or hit in order to push the pin 9a into the pin spacing 44. The pin 9f comprises two parallel legs 92f, 92f', each connected to the body 97f. The legs may be resilient, but do not need to be. Hereby, the pin 9f is provided as a split pin similar to the pin 9a, wherein the split is provided between the two legs 92f, 92f'. Similar to the pin 9a, the legs 92f, 92f' are arranged at a distance from each other, and a wire guide 94*f* is located between the resilient legs 92*f*, 92*f'*, the wire guide 94*f* extending through the pin 9*f* and being defined by a rounded surface at a top and being open at a bottom, an opening of the wire guide 94*f* opening into the split. Alternatively, the wire guide may be provided as a channel as in pins 9*b* to 9*e*. A length of each of the resilient legs 92*f*, 92*f'* is approximately 6 mm. The legs are identical and oppositely positioned to each other.

The pin 9*f* comprises an arm 98 and integral with the body 97*f* and extending from the body 97*f* in a radial direction normal to a longitudinal or length direction of the pin 9*f*. The arm 98 extends to be substantially straight in the lateral direction. The control element 4 comprises a track 49 defined by lateral arm supports in the form of track walls 49*a*, 49*b* with inner surfaces, which extend in a rounded shape where they extend directly above the pin spacing 44 in order to provide spacing for insertion of the pin 9*f*.

FIGS. 7*a* to 7*c* show sequential steps of insertion of the pin 9*f* to attach the steering wire 5 second wire portion 52 to the control element 4 as explained in the following.

As shown in In FIG. 7*a*, the second wire portion 52 is positioned in the track 49, and the pin 9*f* is positioned so that second wire portion 52 is positioned in the wire guide 94*f*, the bottom of the pin 9*f* being positioned at an entrance into the pin spacing 44. The pin 9*f* with arm 98 is positioned in an initial rotary position.

As shown in FIG. 7*b*, the pin 9*f* is then rotated about 90 degrees in a counter-clockwise direction, by means of turning the arm 98, to assume a rotated position as shown. The second wire portion 52 is hereby pulled to extend at least partly around the pin 9*f*, specifically one section of the wire portion 52 around an outer surface of each of the legs 92*f*, 92*f'*, as shown. Hereby, the parts of the second wire portion 52 that extend around the pin 9*f* are clamped between the pin 9*f* and the inner wall of the pin spacing 44 when the pin 9*f* is inserted into the pin spacing 44 as shown in FIG. 7*c* and explained immediately below.

As shown in FIG. 7*c*, the pin 9*f* is then introduced into its final position in the pin spacing 44 so that the second wire portion 52 is at least partly positioned within the pin spacing 44.

The arm 98 may then subsequently be released (not shown). The tension of the tensioned steering wire 5 will then pull the arm 98 in a clockwise direction opposite the direction in which the arm 98 was rotated so that the steering wire 5 tension pushes the arm 98 against the inner surface of the track wall 49*b* so as to prevent the arm 98 from rotating further in the clockwise direction and fixate the pin 9*f* in the pin spacing 44. The steering wire 5 tension thus contributes to fixation of the pin 9*f* in the pin spacing 44. Furthermore, a larger part of the steering wire 5 second portion 52 is clamped between the pin 9*f* and the wall of the pin spacing 44 than in the previous embodiments, which provides a stronger fixation of the steering wire 5.

The pin 9*f* may be combined with one of the above pins 9*a* to 9*e* comprising one or more pin snap parts. Thus, the pin snap parts, head, resilient legs, barbs and/or associated snap parts of one of the embodiments of FIGS. 3 and 6*a* to 6*d* may be included in the pin 9*f*. After the arm 98 is rotated, when the pin 9*f* is pushed into the final, inserted position, a pin snap part of the pin 9*f* may then snap into the associated snap part of the control element 4. Hereby, fixation of the pin 9*f* in the pin spacing 44 may be further improved. Alternatively, or additionally, a pin snap part may be included in the arm 98, e.g. at a bottom thereof, which in a manner similar to the above described snap parts of the pins 9*a* to 9*e* may snap into an associated snap part of the control element 4, e.g. provided as a barb on the inner surface of the track wall 49*b*. In another or additional variation, the pin 9*f* comprises a head, such as similar to the head of the previous embodiments. The head (or the top surface 96*f* of the pin 9*f*, i.e. if no head is present) may comprise an indentation or the like for a rotating tool, such as a screwdriver slot for a screwdriver, for affecting rotation of the pin 9*f*, in which case the indentation or the like may replace or supplement the arm 98. This head may comprise one or two or more flat lateral surfaces, e.g. be rectangular in cross section or round in cross section with one or two chamfered surfaces. One flat surface may match one of the inner surfaces of the walls 49*a*, 49*b* in the initial position of the pin as shown in FIG. 7*a*, which may be flat too, i.e. not be rounded in the area of the pin as shown in FIGS. 7*a* to 7*c*. The head and/or one of the walls 49*a*, 49*b* may further have enough flexibility to allow the head and pin to overcome the resistance between the head when being rotated, A lateral surface of the pin facing the wall in the initial position may be round to ease turning. A lateral surface of the pin facing the wall after the pin has been turned may be a flat surface facing or abutting a flat inner surface of the wall. The head and/or wall may then substantially return to the undeformed initial position after having been rotated, whereby a snapping function may be achieved when turning the pin and the flat surfaces face each other. The resistance between the pin and the flat surface of the wall may then provide resistance against the pin rotating back to the initial position, e.g. a resistance between a corner or edge of the flat surface of the pin and the flat inner surface of the wall, whereby a rotation lock may be achieved. In such embodiments, the pin may be inserted completely into the pin spacing before being rotated.

The skilled person will appreciate that a number of further embodiments of the pin 9 and wall 45 may be envisioned within the scope of the present invention. For instance, the wire guide 47*a* may be provided as a surface recess of the wall 45 on one side of the pin 9 and continue as a through-hole extending through the wall 45 on the other side of the pin 9.

List of references:

| PART NUMBER | PART DESCRIPTION |
| --- | --- |
| 1 | endoscope |
| 2 | operating handle |
| 3 | insertion tube |
| 31 | proximal end |
| 32 | distal end |
| 33 | steerable tip part |
| 33a | first direction |
| 33b | second direction |
| 4 | control element |
| 41 | operating member |
| 42 | lever |
| 43 | axis |
| 44 | pin spacing |
| 45 | wall |
| 46 | wall corner |
| 47 | wire guide |
| 48 | associated snap part |
| 49 | track |
| 5 | steering wire |
| 5a, 5b | direction |
| 5c | angle |
| 52 | second wire portion |
| 53 | third wire portion |
| 6 | wire support |
| 7 | adhesive |
| 9 | pin |

-continued

List of references:

| PART NUMBER | PART DESCRIPTION |
| --- | --- |
| 91 | pin snap part |
| 92 | resilient leg |
| 93 | barb |
| 94 | wire guide |
| 95 | pin corner |
| 96 | head |
| 97 | body |
| 98 | arm |

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

We claim:

1. A method for fixation of a wire portion of an endoscope, the method comprising:
   a) providing:
      an operating handle;
      an insertion tube with a proximal end and a distal end, and with a steerable tip part located at the distal end;
      a control element movable in relation to the operating handle, the control element having at least one wall, a rotation axis, a lever extending from the rotation axis through a shell of the operating handle, a control member connected to the lever and operable to rotate the control element, and a pin spacing defined in the at least one wall of the control element;
      a pin comprising a wire guide; and
      a steering wire having a first wire portion connected to the steerable tip part, a second wire portion, and a third wire portion, the second wire portion being located between the first and third wire portions;
   b) pulling the third wire portion so as to tension the steering wire; and
   c) inserting the pin into the pin spacing so that the second wire portion is positioned in the wire guide and is clamped between the pin and the at least one wall of the control element, whereby the pin and the second wire portion are fixated to the control element so as to maintain a wire tension between the first and second wire portions.

2. The method of claim 1, wherein step a) further comprises providing a wire support, in which the steering wire is guided, and which is fixated to the operating handle, and wherein in step b) the steering wire extends along a first direction from an exit from the wire support, and wherein a pulling force exerted on the third wire portion extends in a second direction, an angle between the first and second directions being less than 120°.

3. The method of claim 1, further comprising: d) applying an adhesive to the second wire portion, in the pin spacing and/or on the pin.

4. The method of claim 1, wherein the pin comprises a pin snap part, and the pin spacing comprises an associated pin snap part, and wherein step c) comprises inserting the pin into the pin spacing so that the pin snap part snaps into engagement with the associated snap part.

5. The method of claim 4, wherein the pin snap part and/or the associated snap part comprises at least one resilient leg with a barb, wherein in step c), during insertion of the pin into the pin spacing, the resilient leg is deflected from a resting position, and, after insertion of the pin into the pin spacing, the resilient leg returns towards the resting position so that the barb snaps into engagement with the other of the pin snap part and the associated snap part.

6. The method of claim 5, wherein the pin snap part comprises two resilient legs, each having a barb, the resilient legs being arranged at a distance from each other, and a wire guide being located between the resilient legs.

7. The method of claim 1, wherein in step c) the second wire portion is fixated by bending the second wire portion around at least one corner or edge of the pin and/or the wall so as to form at least one wire step.

8. The method of claim 1, wherein step a) further comprises providing a first wire guide, which is fixated to the control element, the first wire guide being provided adjacent to the pin spacing, and wherein step c) further comprises guiding the steering wire through the first wire guide.

9. The method of claim 1, wherein the steering wire is a first steering wire, the pin is a first pin, and the pin spacing is a first pin spacing, and wherein step a) further comprises:
   providing a second steering wire having a first wire portion connected to the steerable tip part, a second wire portion and a third wire portion, the second wire portion being located between the first and third wire portions; and
   providing a second pin with a snap part and a second pin spacing with an associated pin snap part; and
   wherein the method further comprises the step, which is performed simultaneously with step b), of pulling the third wire portion of the second steering wire so as to tension the second steering wire; and
   wherein the method further comprises the step, which is performed simultaneously with step c), of inserting the second pin into the second pin spacing so that the pin snap part snaps into engagement with the associated snap part,
   whereby the second pin and the second wire portion are fixated to the control element so as to maintain a second wire tension between the first and second wire portions.

10. The method of claim 1, wherein the pin comprises an arm, and wherein, before or during step c), the pin is rotated by means of the arm to assume a rotated position, wherein the arm maintains the pin in the rotated position when the pin is inserted into the pin spacing.

11. An endoscope comprising:
   an operating handle;
   an insertion tube with a proximal end and a distal end, and with a steerable tip part located at the distal end;
   a control element movable in relation to the operating handle, the control element having a pin spacing defined by at least one wall of the control element;
   at least one tensioned steering wire having a first wire portion connected to the steerable tip part and a second wire portion connected to the control element, the steering wire being tensioned between the first and second wire portions; and
   a pin located in the pin spacing, the pin comprising a wire guide and a portion of the wire being located in the wire guide,
   wherein the second wire portion is connected to the control element by being clamped between the pin and the at least one wall of the control element so that the second wire portion is fixated in relation to the control element.

12. The endoscope according to claim 11, wherein a hardened adhesive adheres the second wire portion to the at least one wall and/or to the pin.

13. The endoscope of claim 11, wherein the pin and/or the at least one wall comprises at least one corner or edge, and wherein the second wire portion is bent around the at least one corner or edge so as to form at least one wire step.

14. The endoscope of claim 11, further comprising a first wire guide fixated to the control element adjacent to the pin spacing, wherein the steering wire passes through the first wire guide.

15. The endoscope of claim 11, wherein the steering wire is a first steering wire, and the pin is a first pin, the pin spacing is a first pin spacing, wherein the control element further has a second pin spacing defined by at least one wall of the control element; and wherein the endoscope further comprises:
   a second tensioned steering wire having a first wire portion connected to the steerable tip part, and a second wire portion connected to the control element, the steering wire being tensioned between the first and second wire portions; and
   a second pin located in the second pin spacing;
   wherein the second wire portion of the second steering wire is connected to the control element by being clamped between the second pin and the at least one wall of the control element so that the second wire portion is fixated in relation to the control element.

16. The endoscope of claim 11, wherein the pin comprises a pin snap part, and the pin spacing comprises an associated pin snap part, and the pin is inserted into the pin spacing and the pin snap part is engaged with the associated snap part.

17. The endoscope of claim 16, wherein the pin snap part or the associated snap part comprises at least one resilient leg with a barb engaged with the other of the pin snap part and the associated snap part.

18. The endoscope of claim 17, wherein the pin snap part comprises two resilient legs, each having a barb, the resilient legs being arranged at a distance from each other, and wherein a wire guide is located between the resilient legs.

* * * * *